(12) United States Patent
Hamamoto

(10) Patent No.: US 7,032,448 B2
(45) Date of Patent: Apr. 25, 2006

(54) CAPACITIVE HUMIDITY SENSOR

(75) Inventor: Kazuaki Hamamoto, Nagoya (JP)

(73) Assignee: Denso Corporation, Kariya (JP)

( * ) Notice: Subject to any disclaimer, the term of this patent is extended or adjusted under 35 U.S.C. 154(b) by 33 days.

(21) Appl. No.: 10/797,117

(22) Filed: Mar. 11, 2004

(65) Prior Publication Data

US 2004/0182153 A1    Sep. 23, 2004

(30) Foreign Application Priority Data

Mar. 19, 2003   (JP)   ............................. 2003-075017

(51) Int. Cl.
*G01N 27/22* (2006.01)
*G01R 27/26* (2006.01)

(52) U.S. Cl. ................. 73/335.04; 73/29.01; 73/29.05; 73/335.02; 361/280; 361/281; 361/286

(58) Field of Classification Search .............. 73/29.01, 73/29.05, 31.05, 31.06, 335.02, 335.04; 361/280, 361/281, 286, 303; 422/83, 98
See application file for complete search history.

(56) References Cited

U.S. PATENT DOCUMENTS

| | | | | |
|---|---|---|---|---|
| 3,891,958 A * | 6/1975 | Wakabayashi | ................ | 338/35 |
| 4,393,434 A * | 7/1983 | Imai et al. | ................... | 361/286 |
| 4,419,888 A * | 12/1983 | Kitamura et al. | ......... | 73/335.05 |
| 4,473,813 A * | 9/1984 | Kinjo et al. | .................... | 338/35 |
| 4,603,372 A * | 7/1986 | Abadie et al. | .............. | 361/286 |
| 5,004,700 A * | 4/1991 | Webb et al. | .................... | 438/49 |
| 5,036,704 A * | 8/1991 | Pusatcioglu et al. | ..... | 73/335.02 |
| 5,050,434 A * | 9/1991 | Demisch | .................. | 73/335.04 |
| 5,254,371 A * | 10/1993 | Hegner et al. | ............ | 427/126.3 |
| 5,741,540 A * | 4/1998 | Li et al. | .................... | 427/126.3 |
| 5,767,687 A * | 6/1998 | Geist | ........................... | 324/664 |
| 5,837,884 A * | 11/1998 | Kimura et al. | ............. | 73/25.04 |
| 5,855,849 A * | 1/1999 | Li et al. | ........................ | 422/88 |
| 6,229,318 B1 * | 5/2001 | Suda | ........................... | 324/696 |
| 6,342,295 B1 * | 1/2002 | Kobayashi | ................... | 428/323 |
| 6,445,565 B1 * | 9/2002 | Toyoda et al. | ............... | 361/303 |
| 6,580,600 B1 | 6/2003 | Toyoda et al. | | |
| 6,615,659 B1 * | 9/2003 | Shibue et al. | ............. | 73/335.02 |
| 6,840,103 B1 * | 1/2005 | Lee et al. | ................. | 73/335.05 |
| 2001/0015089 A1 * | 8/2001 | Kleinhans et al. | ............ | 73/23.2 |
| 2003/0002238 A1 * | 1/2003 | Toyoda | ......................... | 361/302 |
| 2003/0010119 A1 * | 1/2003 | Toyoda | ..................... | 73/335.04 |

FOREIGN PATENT DOCUMENTS

| | | |
|---|---|---|
| GB | 2194845 A * | 3/1988 |
| WO | WO 9103734 A1 * | 3/1991 |
| WO | WO 200142775 A1 * | 6/2001 |

* cited by examiner

*Primary Examiner*—Hezron Williams
*Assistant Examiner*—David A. Rogers
(74) *Attorney, Agent, or Firm*—Posz Law Group, PLC

(57) ABSTRACT

A capacitive humidity sensor includes a detection portion and a reference portion. The detection portion includes detection electrodes and a moisture sensitive film. The reference portion includes reference electrodes and a moisture permeation film as a capacitance adjusting film. The capacitive humidity sensor detects humidity by converting a capacitance difference between a capacitance of the detection electrodes and a capacitance of the reference electrodes to an electric signal by using a capacitance-voltage conversion circuit. The moisture permeation film reduces offset voltage of the capacitive humidity sensor. Thus, an offset compensation circuit or the like is not required.

10 Claims, 3 Drawing Sheets

CAPACITIVE HUMIDITY SENSOR

CROSS REFERENCE TO RELATED APPLICATION

This application is based on Japanese Patent Application No. 2003-75017 filed on Mar. 19, 2003, the disclosure of which is incorporated herein by reference.

BACKGROUND OF THE INVENTION

1. Field of the Invention

The present invention relates to a capacitive humidity sensor, which has a capacitance adjusting film in a reference portion in order to reduce offset voltage of the sensor.

2. Description of Related Art

A capacitive humidity sensor, which detects humidity based on a change of capacitance between two detection electrodes provided on a semiconductor substrate, is disclosed in U.S. Pat. No. 6,580,600 B2 (corresponding to JP-A-2002-243690).

This sensor has two detection electrodes, which oppose each other, on a first insulation film formed on a surface of a semiconductor substrate. The detection electrodes are covered with a second insulation film and are further covered with a moisture sensitive film thereon. In addition, a reference portion, having a reference capacitance which does not change even when humidity changes, is provided on the semiconductor substrate.

The detection electrodes and a circuit element portion including the reference portion construct a switched capacitor (SC) circuit. The SC circuit converts a change of capacitance between the detection electrodes to a voltage signal and outputs it. Accordingly, humidity can be detected based on a difference between the reference capacitance and a capacitance of the detection electrodes, which changes according to humidity.

In this capacitive humidity sensor, the reference portion includes the semiconductor substrate and a wiring electrode provided on the semiconductor substrate. The first insulation film, whose permittivity is different from that of the moisture sensitive film, is disposed between the semiconductor substrate and the wiring electrode. In this case, an initial capacitance difference, that is, a difference between the reference capacitance and the capacitance of the detection electrodes in a reference humidity condition (e.g., 0% RH or 100% RH) is large. This causes offset voltage. When this offset voltage is large, an output range based on a humidity change is reduced in a whole output range of the sensor. As a result, accuracy of humidity detection deteriorates. Therefore, the offset voltage needs to be reduced as much as possible.

However, troublesome countermeasures are required in order to reduce the offset voltage in this capacitive humidity sensor. For example, a pattern of the wiring electrode in the reference portion must be enlarged in order to increase an area where the reference portion faces the semiconductor substrate. Otherwise, an offset compensation circuit must be provided in the circuit element portion in order to compensate for the offset voltage. These countermeasures require an additional design of the wiring electrode or the offset compensation circuit. Further, it is difficult to reduce size of the sensor because an area where the circuit element portion is formed is enlarged.

SUMMARY OF THE INVENTION

In view of the foregoing problems, it is an object of the present invention to provide a capacitive humidity sensor which can reduce offset voltage easily and can be reduced in size.

In order to achieve the above objects, a capacitive humidity sensor includes a semiconductor substrate, a detection portion and a reference portion. The detection portion includes a pair of detection electrodes disposed to oppose each other on the semiconductor substrate, and a moisture sensitive film disposed on the pair of detection electrodes. A capacitance of the moisture sensitive film changes according to humidity. The reference portion includes a pair of reference electrodes disposed to oppose each other on the semiconductor substrate. The capacitive humidity sensor detects humidity by converting a difference between a capacitance of the pair of reference electrodes and a capacitance of the pair of detection electrodes to a voltage signal. Furthermore, in the reference portion, a capacitance adjusting film is provided on the reference electrodes in order to reduce a difference between the capacitance of the pair of reference electrodes and the capacitance of the pair of detection electrodes when humidity is in a reference humidity condition.

Thus, the capacitive humidity sensor includes the capacitance adjusting film on the reference electrodes in order to reduce the capacitance difference in the reference humidity condition (e.g., 0% RH or 100% RH), that is, an initial capacitance difference. Therefore, the initial capacitance difference between the capacitance of the detection electrodes and the capacitance of the reference electrodes can be reduced. That is, offset voltage can be reduced.

Accordingly, the offset voltage can be reduced easily because it is only required to provide the capacitance adjusting film in the reference portion. Furthermore, the sensor can be reduced in size because an offset compensation circuit or enlarging a pattern of the reference electrodes is not required.

BRIEF DESCRIPTION OF THE DRAWINGS

Additional objects and advantages of the present invention will be more readily apparent from the following detailed description of preferred embodiments when taken together with the accompanying drawings, in which.

DETAILED DESCRIPTION OF THE PRESENTLY PREFERRED EMBODIMENTS (First Embodiment)

A capacitive humidity sensor according to the first embodiment is used for detecting indoor humidity for a humidity control of an air conditioner, detecting outdoor humidity for weather observation or the like.

Figure 1:
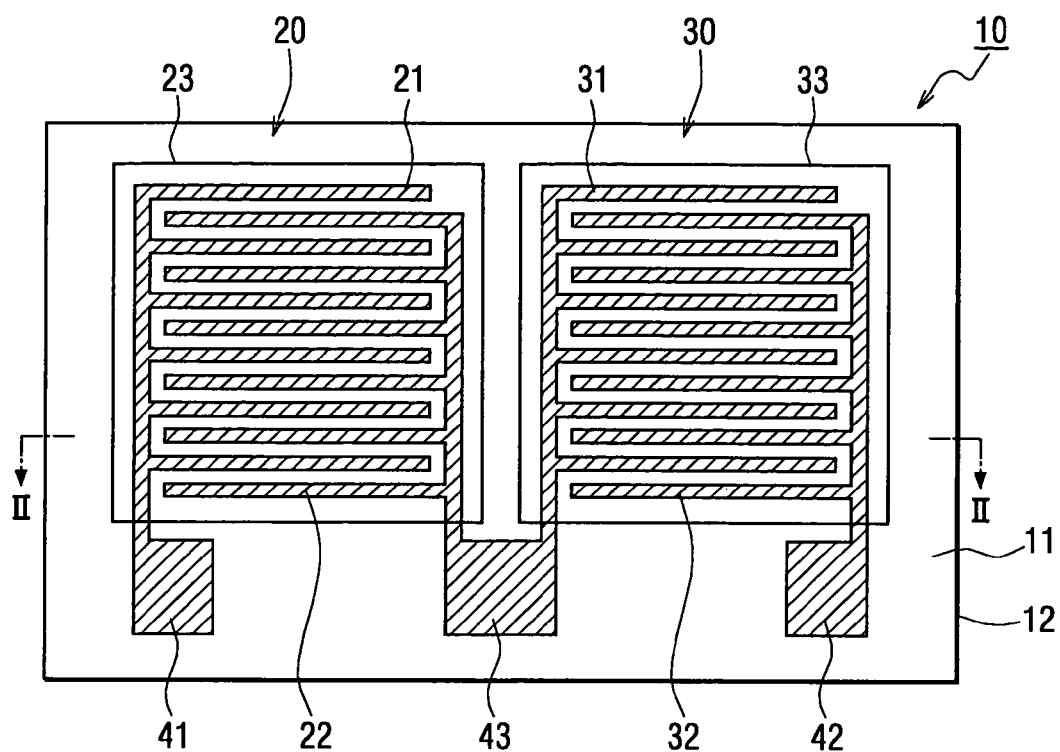
FIG. 1 is a schematic plan view showing a capacitive humidity sensor according to a first embodiment of the present invention.
Figure 2:
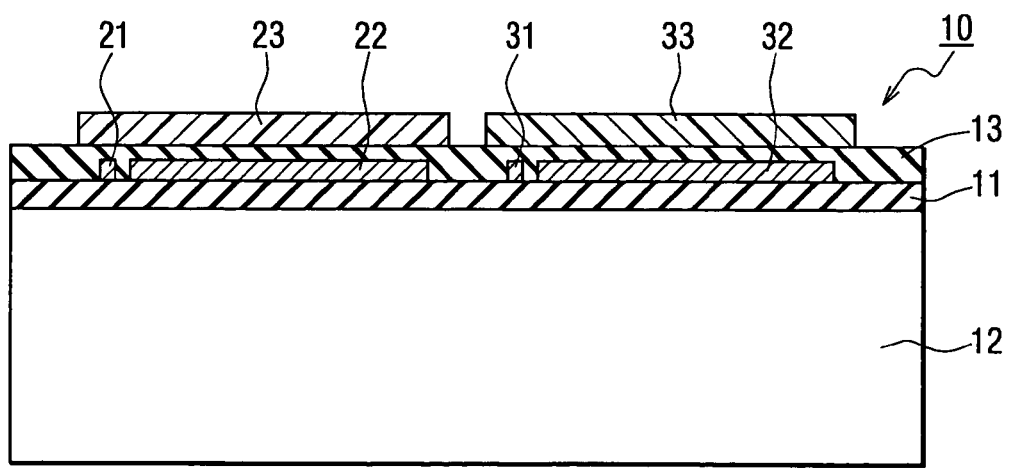
FIG. 2 is a cross-sectional view taken along line II—II in FIG. 1.

In a capacitive humidity sensor 10 shown in FIGS. 1 and 2, a first insulation film 11 is formed on a semiconductor substrate 12. A sensor portion is formed on the first insulation film 11. The sensor portion includes a detection portion 20 and a reference portion 30. The capacitive humidity sensor 10 detects humidity based on a difference between a capacitance of the detection portion 20 and a capacitance of the reference portion 30.

The semiconductor substrate 12 is made of single crystal silicon or the like. A silicon oxide film is formed as the first insulation film 11 on the surface of the semiconductor substrate 12. Furthermore, a pair of detection electrodes 21, 22, which oppose each other, is formed on the first insulation film 11.

The detection electrodes 21, 22 are formed by using an electrically-conductive material (e.g., Al, Ti, Au, Cu) which can be used in a normal semiconductor manufacturing process. In the first embodiment, Al is used. Further, the detection electrodes 21, 22 are comb-shaped although their shape is not limited to a particular shape. The detection electrodes 21, 22 are interleaved so that each tooth portion of one of the detection electrodes 21, 22 is interposed between corresponding tooth portions of the other of the detection electrodes 21, 22. Thus, an area where the detection electrodes 21, 22 are disposed can be reduced as much as possible while an area where the detection electrodes 21, 22 oppose each other can be increased. Therefore, a capacitance of the whole of the detection electrodes 21, 22, that is, a capacitance of the detection portion 20 can be increased. Further, a detection electrode pad 41 is formed on an end of the detection electrode 21. The detection electrode pad 41 is made of the same material as that of the detection electrodes 21, 22. A predetermined voltage is applied to the detection electrode pad 41.

The reference portion 30 includes reference electrodes 31, 32. The reference electrodes 31, 32 are formed to oppose each other on the same plane as that of the detection electrodes 21, 22 of the detection portion 20. Similarly to the detection electrodes 21, 22, the reference electrodes 31, 32 are formed by using the electrically-conductive material which can be used in a normal semiconductor manufacturing process. In the first embodiment, Al is used similarly to the detection electrodes 21, 22. In the first embodiment, although a shape of the reference electrodes 31, 32 is not limited to a particular shape, a pattern (shape and size) of the reference electrodes 31, 32 is substantially equal to that of the detection electrodes 21, 22. Accordingly, an area where the reference electrodes 31, 32 are disposed can be reduced as much as possible while an area where the reference electrodes 31, 32 oppose each other can be increased. Therefore, a capacitance of the whole of the reference electrodes 31, 32, that is, a capacitance of the reference portion 30 can be increased. Further, a reference electrode pad 42 is formed on an end of the reference electrode 32. The reference electrode pad 42 is made of the same material as that of the reference electrodes 31, 32. A predetermined voltage is applied to the reference electrode pad 42. Further, a common electrode pad 43 is formed on an end of the detection electrode 22 and the reference electrode 31 by using the same material as that of the other pads 41, 42.

As shown in FIG. 2, a silicon nitride film is formed as a second insulation film 13 on the detection electrodes 21, 22 and the reference electrodes 31, 32. In the first embodiment, the second insulation film 13 covers the detection electrodes 21, 22 and the reference electrodes 31, 32. Further, the second insulation film 13 is interposed between the detection electrodes 21, 22 and between the reference electrodes 31, 32. However, the second insulation film 13 is used in order to ensure insulating performance and humidity resistance of the detection electrodes 21, 22 and the reference electrodes 31, 32. Therefore, it is possible that the second insulation film 13 merely covers the detection electrodes 21, 22 and the reference electrodes 31, 32.

As described above, the first and second insulation films 11, 13 ensure insulating performance. Further, the second insulation film 13 ensures humidity resistance of the electrodes 21, 22, 31, 32. Therefore, reliability of the sensor can be increased when the first and second insulation films 11, 13 are provided in the capacitive humidity sensor 10.

Furthermore, a moisture sensitive film 23 is formed in a region of the detection portion 20 on the second insulation film 13, that is, a region which covers the detection electrodes 21, 22. A capacitance adjusting film 33 is formed in a region of the reference portion 30 on the second insulation film 13, that is, a region which covers the reference electrodes 31, 32.

The moisture sensitive film 23 is made of a hygroscopic macro-molecule organic material such as polyimide or butyric acetylcellulose. In the first embodiment, polyimide is used. When the moisture sensitive film 23 absorbs water molecules, permittivity of the moisture sensitive film 23 changes largely according to an amount of absorbed water molecules. Accordingly, a capacitance Cs between the detection electrodes 21, 22 changes according to the amount of absorbed water molecules in the moisture sensitive film 23.

Further, as shown in FIG. 2, the moisture sensitive film 23 is formed to cover the detection electrodes 21, 22 through the second insulation film 13. However, it is possible that the moisture sensitive film 23 is interposed between the detection electrodes 21, 22 while the moisture sensitive film 23 covers the detection electrodes 21, 22 through the second insulation film 13.

The capacitance adjusting film is provided in order to reduce a difference between the capacitance of the reference electrodes 31, 32 and the capacitance of the detection electrodes 21, 22 in a reference humidity condition (e.g., 0% RH or 100% RH). that is, an initial capacitance difference. For example, a moisture permeation film 33, which causes moisture vapor in gas to permeate and has a constant permittivity, can be used. Specifically, silicone or fluorine gel, Gore-Tex (registered trademark) and the like, which cause only moisture vapor to permeate and block liquid, can be used. In the above materials, silicone gel is preferable because it has superior moisture vapor permeability. In the first embodiment, silicone gel whose permittivity is substantially equal to that of the moisture sensitive film 23 at 0% RH is used, The moisture permeation film 33 is hardly affected by humidity. Therefore, a capacitance Cr of the reference electrodes 31, 32 is almost constant without being affected by humidity. Further, the above reference humidity condition is humidity which is set to a reference when offset voltage is adjusted in the capacitive humidity sensor 10. The reference humidity condition can be freely set within a range from 0% RH to 100% RH. Generally, the reference humidity condition is set to 0% RH or 100% RH.

In the above structure, the capacitive humidity sensor 10 according to the first embodiment includes the detection portion 20 and the reference portion 30 as a sensor portion 40 on the semiconductor substrate 12. The capacitive humidity sensor 10 detects humidity based on a difference between the capacitance Cs of the detection electrodes 21, 22 and the capacitance Cr of the reference electrodes 31, 32.

Figure 3:
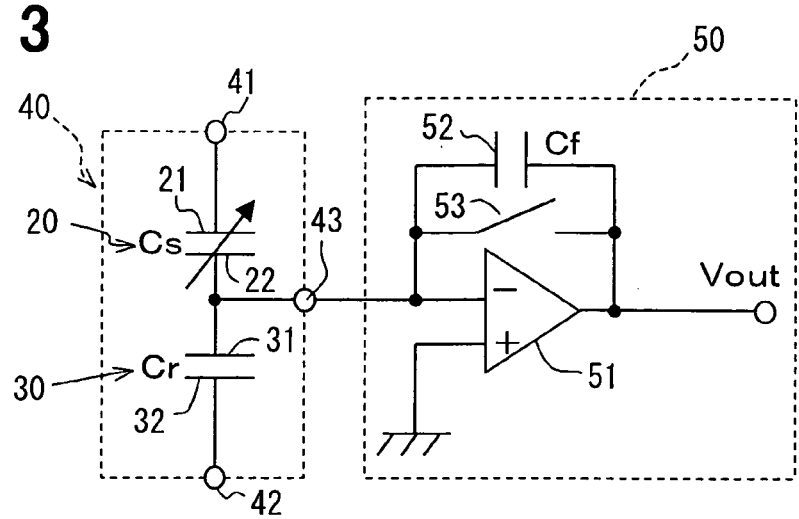
FIG. 3 is a circuit diagram showing a detection circuit of the capacitive humidity sensor.

In the capacitive humidity sensor 10, a detection circuit in FIG. 3 is provided. The detection circuit includes a capacitance-voltage (C-V) conversion circuit 50 which is a switched capacitor circuit. The C/V conversion circuit 50 includes an operational amplifier 51, a capacitor 52 with a capacitance Cf and a switch 53. In the C/V conversion circuit 50, an electric charge Qs is stored between the detection electrodes 21, 22 proportionally to the capacitance Cs. Further, an electric charge Qr is stored between the reference electrodes 31, 32 proportionally to the capacitance Cr. The capacitor 52 stores an electric charge Qf corresponding to a difference between the electric charges Qs and Qr. The C/V conversion circuit 50 converts Qf to voltage and outputs it. Further, the C/V conversion circuit 50 can be integrated into a circuit element portion (not shown) and provided on the semiconductor substrate 12 together with the sensor portion 40. However, it is possible that the C/V conversion circuit 50 is provided as an outside circuit and connected to the common electrode pad 43 in the sensor portion 40.

The inverting input terminal of the operational amplifier 51 is connected to the detection electrode 22 and the reference electrode 31 through the common electrode pad 43.

The capacitor 52 and the switch 53 are connected parallel to each other between the inverting input terminal and the output terminal. Further, the capacitance of the detection portion 20 and the capacitance of the reference portion 30 are substantially equal in the reference humidity condition (0% RH) in the first embodiment. Therefore, the non-inverting input terminal of the operational amplifier 51 is connected to the ground.

The C/V conversion circuit 50 includes a control circuit (not shown). The control circuit inputs a first carrier wave signal, which periodically changes at a constant amplitude Vcc, to the detection electrode 21 of the detection portion 20 from the detection electrode pad 41. Further, the control circuit inputs a second carrier wave signal, whose phase is shifted by 180 degrees relative to the first carrier wave signal and amplitude is Vcc similarly to the first carrier wave signal, to the reference electrode 32 of the reference portion 30 from the reference electrode pad 42.

Further, the switch 53 is turned on or off by a trigger signal synchronized with a clock signal from the control circuit. For example, as shown in FIG. 4, the switch 53 is turned on at a timing when the first carrier wave signal changes from 0 to Vcc and the ON status continues for a constant time (e.g., a time shorter than a half of ON period of the first carrier wave signal).

Figure 4:
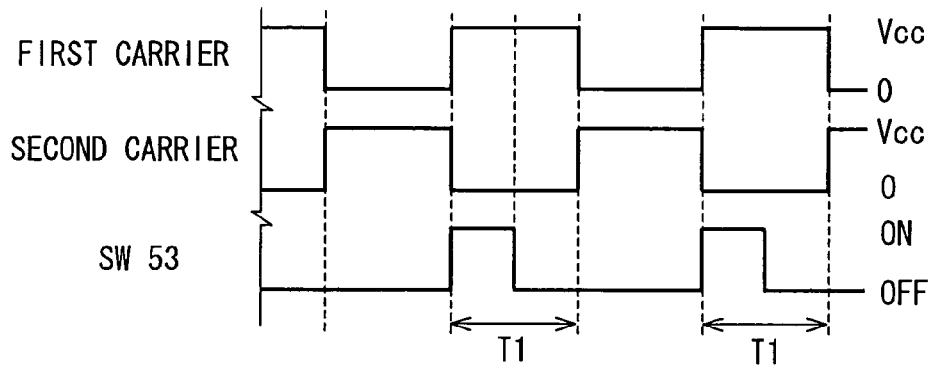
FIG. 4 is a timing chart showing signal changes of the detection circuit.

As shown in FIG. 4, when the switch 53 is turned on during a detection time period T1, an electric charge of the capacitor 52 is discharged. Then, after the switch 53 is turned off, an electric charge (Cs−Cr)×Vcc is discharged from the detection electrodes 21, 22 and the reference electrodes 31, 32. The discharged electric charge (Cs−Cr)×Vcc is stored in the capacitor 52. Accordingly, voltage Vout develops in the output terminal of the operational amplifier 51. Vout depends on a capacitance difference (Cs−Cr) of the sensor portion 40 and the voltage amplitude Vcc. Specifically, Vout is $$V\text{out}=(Cs-Cr)\times Vcc/Cf \tag{1}$$

The capacitance Cs of the detection portion 20 changes according to a humidity change in the environment. However, the capacitance Cr of the reference portion 30 does not change. Accordingly, humidity can be detected by detecting Vout in the formula (1). Further, the voltage Vout is processed by a signal processing circuit (not shown) including an amplifying circuit and a low-pass filter and is detected as a humidity detection signal.

In manufacturing the capacitive humidity sensor 10, a silicon oxide film as the first insulation film 11 is formed first on the semiconductor substrate 12 by chemical vapor deposition (CVD) method or the like.

Secondly, the detection electrodes 21, 22 and the reference electrodes 31, 32 are formed on the first insulation film 11 by using Al or the like based on evaporation method or the like. At the same time, the detection electrode pad 41, the reference electrode pad 42 and the common electrode pad 43 are formed. Then, a silicon nitride film as the second insulation film 13 is formed by using plasma CVD method or the like, in order to cover the detection electrodes 21, 22 and the reference electrodes 31, 32.

Thirdly, when at least one of the detection electrode pad 41, the reference electrode pad 42 and the common electrode pad 43 is connected to the outside circuit or the like, the second insulation film 13 is partially removed on the pad by etching using photolithography.

Then, the moisture sensitive film 23 is formed in a region of the detection portion 20 on the second insulation film 13 by a method that a predetermined pattern is printed by printing method and is hardened, or a method that polyimide is coated by spin coating, is hardened and is patterned by photo-etching.

Further, the moisture permeation film 33 is formed by coating silicone gel in a region of the reference portion 30 on the second insulation film 13 by using potting or the like. When the circuit element portion such as the C/V conversion circuit 50 is formed on the semiconductor substrate 12, the circuit element portion is formed by using a normal semiconductor manufacturing technique before the first insulation film 11 is formed.

Figure 5:
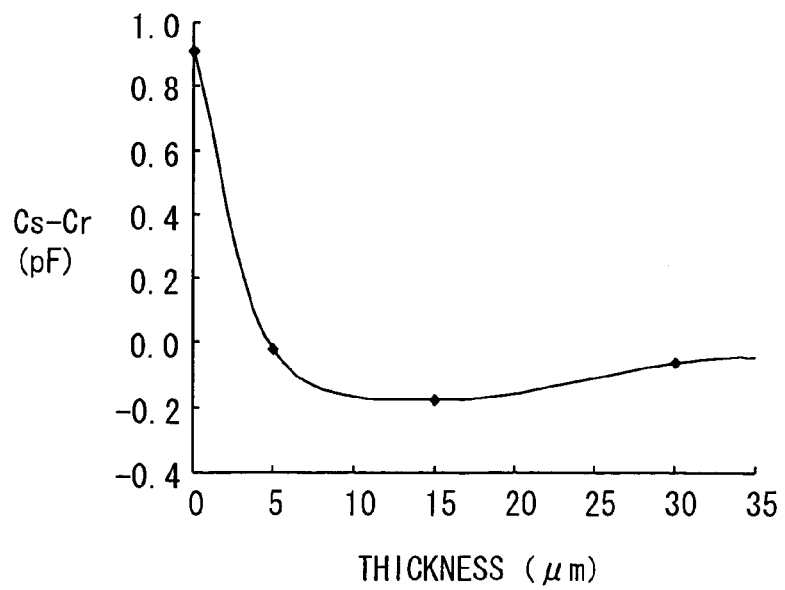
FIG. 5 is a simulation result showing a relationship between a thickness of a moisture permeation film and an initial capacitance difference.

In the capacitive humidity sensor 10 manufactured as described above, the moisture permeation film 33 as the capacitance adjusting film has an effect on reduction in the initial capacitance difference (offset voltage). A simulation result in FIG. 5 shows this effect clearly. In the simulation, a structure of the sensor is the same as that of the above capacitive humidity sensor 10. Polyimide with permittivity 3.4 at 0% RH is assumed as the moisture sensitive film 23 and silicone gel with permittivity 3.2 is assumed as the moisture permeation film 33. FIG. 5 shows that the initial capacitance difference (Cs−Cr) between the detection portion 20 and the reference portion 30 at 0% RH can be reduced by providing the moisture permeation film 33 on the reference electrodes 31, 32.

Furthermore, an experiment was actually performed in order to compare the above capacitive humidity sensor 10 and a capacitive humidity sensor without the moisture permeation film 33. An initial capacitance difference of the capacitive humidity sensor 10 with the moisture permeation film 33 is about ⅛ of that of the sensor without the moisture permeation film 33.

Here, it is assumed that a sensor output range is from 0 to 5 V. If offset voltage of 2 V develops, only 3 V is used for an output range of humidity detection. Therefore, accuracy of humidity detection deteriorates. In order to compensate for the offset voltage and improve detection accuracy, it is possible that an offset compensation circuit is provided or the reference electrodes 31, 32 are enlarged.

However, in the capacitive humidity sensor 10 according to the first embodiment, the capacitance adjusting film is provided as a part of the sensor portion 40 on the reference electrodes 31, 32. Thus, the initial capacitance difference can be reduced and the offset voltage can be reduced easily. Accordingly, the offset compensation circuit or enlarging a pattern of the reference electrodes 31, 32 in the reference portion 30 is not required. Therefore, the capacitive humidity sensor 10 can be reduced in size.

When an electrode pattern of the detection electrodes 21, 22 and an electrode pattern of the reference electrodes 31, 32 are substantially equal, the reference electrodes 31, 32 do not need to be designed newly. Therefore, a manufacturing process can be simplified because the electrodes 21, 22, 31, 32 can be formed at the same time.

When permittivity of the moisture permeation film 33 in the reference humidity condition (e.g., 0% RH) is larger than that of the moisture sensitive film 23, the initial capacitance difference can be reduced by reducing an electrode pattern of the reference electrodes 31, 32. In this case, pattern designing of the reference electrodes 31, 32 is required although the capacitive humidity sensor 10 can be further reduced in size. Thus, it is preferable that electrode patterns of the electrodes 21, 22, 31, 32 are substantially equal in order to avoid an additional designing of the electrode patterns, although it is not necessarily required.

In the first embodiment, the moisture permeation film 33, whose permittivity is substantially equal to that of the moisture sensitive film 23 at 0% RH, is used. Thus, the initial capacitance difference at 0% RH can be reduced, so that the offset voltage can be reduced. However, the moisture permeation film 33, whose permittivity is substantially equal to that of the moisture sensitive film 23 at 100% RH, can be also used in order to reduce the initial capacitance difference at 100% RH to reduce the offset voltage. In this case, an ON/OFF timing of the switch 53 needs to be modified. Specifically, the switch 53 is turned on at a timing when the second carrier wave signal changes from 0 to Vcc and the ON status continues for a constant time. In addition, it is possible that the reference humidity condition is set to 50% RH.

In the first embodiment, the non-inverting terminal of the operational amplifier 51 is grounded in order to increase the output range of the capacitive humidity sensor 10. However, a predetermined voltage can also be inputted as reference voltage. For example, the initial capacitance difference is reduced as much as possible by adjusting size or thickness of the capacitance adjusting film. Nevertheless, the initial capacitance difference may be caused. In this case, it is possible that voltage developed in the reference condition is inputted to the non-inverting terminal as the reference voltage. Further, when 50% RH is set to the reference humidity condition, Vcc/2 needs to be inputted to the non-inverting terminal.

Figure 6:
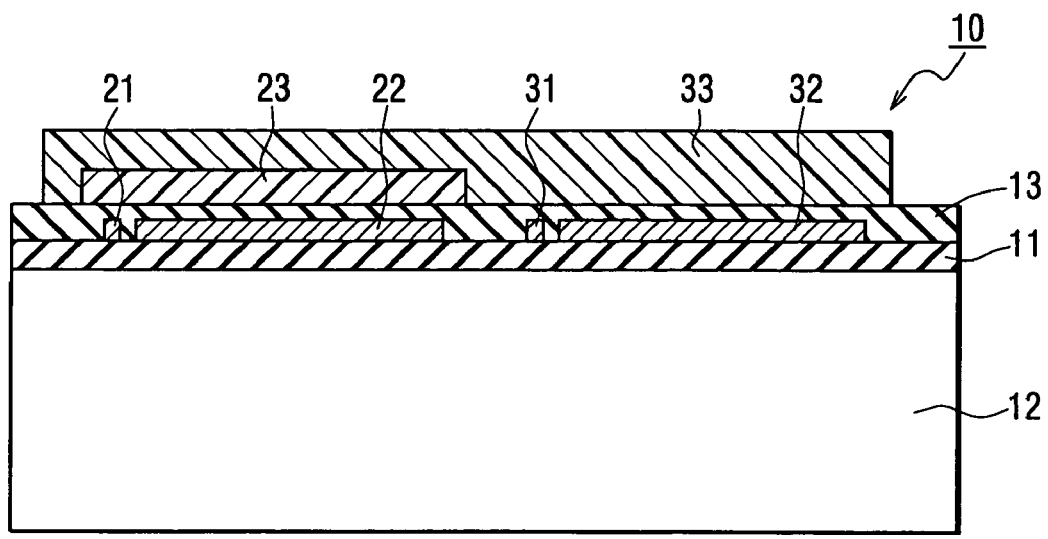
FIG. 6 is a cross-sectional view showing a modified capacitive humidity sensor according to the first embodiment of the present invention.

In the first embodiment, the moisture permeation film 33 is formed as the capacitance adjusting film only on the reference electrodes 31, 32. However, as shown in FIG. 6, the moisture permeation film 33 can be provided in both the detection portion 20 and the reference portion 30 because the moisture permeation film 33 causes moisture to permeate. That is, the moisture permeation film 33 is formed even on the detection electrodes 21, 22 through the second insulation film 13 and the moisture sensitive film 23. In this case, an influence of the moisture permeation film 33 on a capacitance change can be cancelled even if the moisture permeation film 33 is affected by humidity in the environment and permittivity of the moisture permeation film 33 changes. Therefore, humidity can be detected more accurately. Further, the sensor structure can be membrane structure that the semiconductor substrate 12 just under the sensor portion 40 is removed.

(Second Embodiment)

In the first embodiment, the moisture permeation film 33 is used as the capacitance adjusting film. However, in the second embodiment, the moisture sensitive film 23 and a moisture blocking film are formed as the capacitance adjusting film instead of the moisture permeation film 33.

Figure 7:
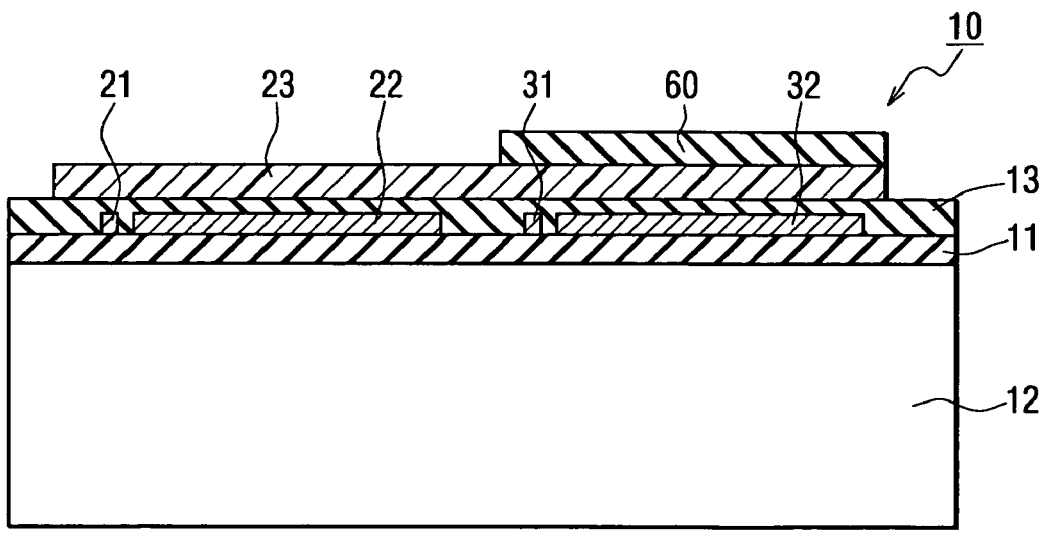
FIG. 7 is a cross-sectional view showing a capacitive humidity sensor according to a second embodiment of the present invention.

As shown in FIG. 7, the detection electrodes 21, 22 and the reference electrodes 31, 32 are formed on the same plane. The silicon nitride film is formed as the second insulation film 13 on these electrodes 21, 22, 31, 32. The patterns of both the detection electrodes 21, 22 and the reference electrodes 31, 32 are substantially equal. In a region of the sensor portion 40 on the second insulation film 13, that is, a region of the detection portion 20 and the reference portion 30, the moisture sensitive film 23 which is made of polyimide or the like is formed.

Accordingly, the capacitance Cs of the detection portion 20 at 0% RH and the capacitance Cr of the reference portion 30 are substantially equal. Therefore, the offset voltage can be almost 0.

Furthermore, on the moisture sensitive film 23 of the reference portion 30, a moisture blocking film 60 is formed. The moisture blocking film 60 is made of a material which does not permeate moisture, that is, block moisture to the moisture sensitive film 23. For example, the silicon oxide film or the silicon nitride film can be used for the moisture blocking film 60. In the second embodiment, the silicon nitride film is used and is formed by plasma CVD method or the like.

Accordingly, permittivity of the moisture sensitive film 23 in the detection portion 20 changes according to a humidity change in the environment and the capacitance Cs of the detection portion 20 changes. To the contrary, permittivity of the moisture sensitive film 23 in the reference portion 30 does not change because the moisture blocking film 60 blocks moisture. Therefore, the capacitance Cr of the reference portion 30 is constant. As described above, in the capacitive humidity sensor 10 according to the second embodiment, the reference portion 30 has the moisture sensitive film 23 as a part of the capacitance adjusting film similarly to the detection portion 20. Therefore, the initial capacitance difference between the capacitance Cs of the detection portion 20 at 0% RH and the capacitance Cr of the reference portion 30 can be reduced. Especially, when the patterns of the detection electrodes 21, 22 and the reference electrodes 31, 32 are equal, the capacitance difference at 0% RH can be almost 0 and the offset voltage can be further reduced.

Further, the reference portion 30 has the moisture blocking film 60 as a part of the capacitance adjusting film on the moisture sensitive film 23. Therefore, the capacitance Cr of the reference electrodes 31, 32 is almost constant even when humidity changes. Accordingly, the capacitive humidity sensor 10 according to the second embodiment can detect humidity accurately.

Further, the offset compensation circuit or enlarging the pattern of the reference electrodes 31, 32 in the reference portion 30 is not required. Only the moisture sensitive film 23 and the moisture blocking film 60 need to be provided as the capacitance adjusting film in the reference portion 30.

Therefore, the offset voltage can be reduced easily and the capacitive humidity sensor 10 can be reduced in size.

Furthermore, when the electrode patterns of the detection electrodes 21, 22 and the reference electrodes 31, 32 are substantially equal, the electrode pattern of the reference electrodes 31, 32 does not need to be designed newly. Therefore, the manufacturing process can be simplified because the electrodes 21, 22, 31, 32 can be formed in the same process at the same time.

The invention claimed is:

1. A capacitive humidity sensor, comprising:
   a semiconductor substrate;
   a detection portion including:
      a pair of detection electrodes disposed to oppose each other on the semiconductor substrate; and
      a moisture sensitive film disposed on the pair of detection electrodes, so that the moisture sensitive film changes a capacitance thereof according to humidity;
   a reference portion including a pair of reference electrodes disposed to oppose each other on the semiconductor substrate;
   a converting means for converting a difference between a capacitance of the pair of reference electrodes and a capacitance of the pair of detection electrodes to an electric signal; and
   a capacitance adjusting gel film disposed on the pair of reference electrodes in order to reduce a difference between the capacitance of the pair of reference electrodes and the capacitance of the pair of detection electrodes in a reference humidity condition,
   wherein the detection electrodes and the reference electrodes are substantially equal in pattern and size; and
   wherein the moisture sensitive film and the capacitance adjusting gel film have substantially equal permittivity in the reference humidity condition.

2. The capacitive humidity sensor according to claim 1, wherein the capacitance adjusting gel film is provided not only in the reference portion but also film of the detection portion.

3. The capacitive humidity sensor according to claim 1, wherein:
   the moisture sensitive film extending to cover not only the detection portion but also the reference portion; and
   a moisture blocking film provided on the moisture sensitive film in the reference portion.

4. The capacitive humidity sensor according to claim 3, wherein the moisture blocking film is a silicon oxide film or a silicon nitride film.

5. The capacitive humidity sensor according to claim 1, wherein:
   the pair of detection electrodes in the detection portion is comb-shaped; and
   each tooth portion of one of the detection electrodes is interleaved between corresponding tooth portions of the other of the detection electrodes.

6. The capacitive humidity sensor according to claim 1, further comprising:
   a first insulation film provided between the detection electrodes and the semiconductor substrate, and between the reference electrodes and the semiconductor substrate; and
   a second insulation film provided between the detection electrodes and the moisture sensitive film, and between the reference electrodes and the capacitance adjusting gel film.

7. A capacitive humidity sensor, comprising:
   a semiconductor substrate;
   a first insulation film formed to cover a surface of the semiconductor substrate;
   a pair of detection electrodes disposed to oppose each other on the first insulation film;
   a pair of reference electrodes disposed to oppose each other on the first insulation film, the pair of reference electrodes being substantially equal to the pair of detection electrodes in pattern and size;
   a converting means for converting a difference between a capacitance of the pair of detection electrodes and a capacitance of the pair of reference electrodes to an electric signal;
   a second insulation film formed to cover the pair of detection electrodes and the pair of reference electrodes;
   a moisture sensitive film disposed on the second insulation film in a region where the pair of detection electrodes is disposed, so that the moisture sensitive film changes a capacitance thereof according to humidity; and
   a moisture permeation film disposed on the second insulation film in a region where the pair of reference electrodes is disposed in order to reduce a difference between the capacitance of the pair of detection electrodes and the capacitance of the pair of reference electrodes in a reference humidity condition, the moisture permeation film having a permittivity substantially equal to a permittivity of the moisture sensitive film in the reference humidity condition.

8. A capacitive humidity sensor, comprising:
   a semiconductor substrate;
   a first insulation film formed to cover a surface of the semiconductor substrate;
   a pair of detection electrodes disposed to oppose each other on the first insulation film;
   a pair of reference electrodes disposed to oppose each other on the first insulation film, the pair of reference electrodes being substantially equal to the pair of detection electrodes in pattern and size;
   a converting means for converting a difference between a capacitance of the pair of detection electrodes and a capacitance of the pair of reference electrodes to an electric signal;
   a second insulation film formed to cover the pair of detection electrodes and the pair of reference electrodes;
   a moisture sensitive film disposed on the second insulation film in a region where the pair of detection electrodes is disposed, so that the moisture sensitive film changes a capacitance thereof according to humidity; and
   a moisture permeation film disposed to cover the moisture sensitive film and the second insulation film in a region where the pair of reference electrodes is disposed in order to reduce a difference between the capacitance of the pair of detection electrodes and the capacitance of the pair of reference electrodes in a reference humidity condition, the moisture permeation film having a per mittivity substantially equal to a permittivity of the moisture sensitive film in the reference humidity condition.

9. A capacitive humidity sensor, comprising:

a semiconductor substrate;

a detection portion including:
- a pair of detection electrodes disposed to oppose each other on the semiconductor substrate; and
- a moisture sensitive film disposed on the pair of detection electrodes, so that the moisture sensitive film changes a capacitance thereof according to humidity;

a reference portion including a pair of reference electrodes disposed to oppose each other on the semiconductor substrate;

a converting means for converting a difference between a capacitance of the pair of reference electrode and a capacitance of the pair of detection electrodes to an electric signal; and a capacitance adjusting gel film disposed on the pair of reference electrodes in order to reduce a difference between the capacitance of the pair of reference electrodes and the capacitance of the pair of detection electrodes in a reference humidity condition.

10. The capacitive humidity sensor according to claim 9 wherein the capacitance adjusting gel film is provided not only in the reference portion but also on the moisture sensitive film of the detection portion.

* * * * *